United States Patent
Klein

(10) Patent No.: US 9,982,093 B2
(45) Date of Patent: May 29, 2018

(54) METHODS FOR PRODUCING NYLON 7

(71) Applicant: EMPIRE TECHNOLOGY DEVELOPMENT LLC, Wilmington, DE (US)

(72) Inventor: Josef Peter Klein, Vashon, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days. days.

(21) Appl. No.: 15/125,571

(22) PCT Filed: Mar. 10, 2014

(86) PCT No.: PCT/US2014/022798
§ 371 (c)(1),
(2) Date: Sep. 12, 2016

(87) PCT Pub. No.: WO2015/137914
PCT Pub. Date: Sep. 17, 2015

(65) Prior Publication Data
US 2017/0002143 A1    Jan. 5, 2017

(51) Int. Cl.
| | | |
|---|---|---|
| *C07D 307/50* | (2006.01) | |
| *C08G 69/04* | (2006.01) | |
| *C07D 307/48* | (2006.01) | |
| *C07D 307/44* | (2006.01) | |
| *C08G 69/08* | (2006.01) | |

(52) U.S. Cl.
CPC ........... *C08G 69/04* (2013.01); *C07D 307/44* (2013.01); *C07D 307/48* (2013.01); *C07D 307/50* (2013.01); *C08G 69/08* (2013.01); *C10L 2200/0469* (2013.01)

(58) Field of Classification Search
CPC ................ C07D 307/48; C07D 307/50; C10L 2200/0469
See application file for complete search history.

(56) References Cited

U.S. PATENT DOCUMENTS 4,683,298 A      7/1987  Yalpani
2010/0317822 A1  12/2010 Boussie et al.

FOREIGN PATENT DOCUMENTS

| GB | 924422 A | 4/1963 |
| WO | 2013003744 A2 | 1/2013 |
| WO | WO 2013/146085 | * 2/2013 |

OTHER PUBLICATIONS

Papadogianakis et al Catalytic conversions in water. Part 4 ' : Carbonylation of 5-ydroxymethylfurfural (HMF) and benzyl alcohol catalyzed palladium trisulfonated triphenylphosphine complexes, Journal of Molecular Catalysis A: Chemical 116 (1997) 179-190, published on Jan. 1997.*
Buntara et al Caprolactam from Renewable Resources: Catalytic Conversion of 5-Hydroxymethylfurfural into Caprolactone, Angew. Chem. Int. Ed. 2011, 50, 7083-7087, published on Nov. 2011.*
Dangerfield et al., Protecting-group-free synthesis of amines: Synthesis of primary amines from aldehydes via reductive amination, Journal of Organic Chemistry (Jul. 28, 2010), 75(16) pp. 5470-5477.
Estes and Schweizer, Fibers, 4. Polyamide Fibers, Wiley-VCH Verlag GmbH & Co. KGaA (2011), pp. 1-17.
International Search Report and Written Opinion for International Application No. PCT/US14/22798, dated Jun. 16, 2014.
Lewkowski, Synthesis, chemistry and applications of 5-hydroxymethyl-furfural and its derivatives, Archive for Organic Chemistry (Aug. 8, 2005), 2001(1) pp. 17-64.
Lichtenthaler, Carbohydrates as organic raw materials, Ullmann's Encyclopedia of Industrial Chemistry (2012), 6 pp. 583-616.
Mitiakoudis and Gandini, Synthesis and characterization of furanic polyamides, Macromolecules (Feb. 1991), 24(4) pp. 830-835.
Papadogianakis et al., Catalytic conversion in water. Part 4: Carbonylation of 5-hydroxymethylfurfural (HMF) and benzyl alcohol catalysed by palladium trisulfonated triphenylphosphine complexes, Journal of Molecular Catalysis A: chemical (Feb. 24, 1997), 116(1-2) pp. 179-190.
Rosatella et al., 5-Hydroxymethylfurfural (HMF) as a building block platform: Biological properties, synthesis and synthetic applications, Green Chemistry (Feb. 28, 2011), 13(4) pp. 754-793.
Yang et al., Conversion of biomass into 5-hydroxymethyl furfural using solid acid catalyst, Bioresource Technology (Feb. 2011), 102(3) pp. 3424-3429.
Zakrzewska et al., Ionic Liquid-Mediated Formation of 5-Hydroxymethylfurfural—A Promising Biomass-Derived Building Block, Chemical Reviews (2011), 111(2) pp. 397-417.

* cited by examiner

*Primary Examiner* — Gregory Listvoyb

(57) ABSTRACT

Nylon 7 may be produced from biomass derived 6-carbon hydroxymethyl furan compounds as the raw material. The hydroxymethyl furan compounds may be homologated to form an aldehyde that may be aminated to produce an amino carbonyl compound. Hydrogenation/hydro-deoxygenation of the amino-carbonyl compound provides nylon 7.

9 Claims, 2 Drawing Sheets

METHODS FOR PRODUCING NYLON 7

CROSS-REFERENCE TO RELATED APPLICATION

This application is a U.S. national stage filing under 35 U.S.C. § 371 of International Application No. PCT/US2014/022798 filed on Mar. 10, 2014 entitled "METHODS FOR PRODUCING NYLON 7," which is incorporated herein by reference in its entirety.

BACKGROUND

Nylon is a designation for a family of synthetic polymers known as aliphatic polyamides, and is one of the most commonly used classes of polymers. The chemical constituents of nylon include carbon, hydrogen, nitrogen, and oxygen. Types of nylons include nylon 6,6 that may be formed by reacting the 6-carbon diamine, hexamethylenediamine and the 6-carbon dicarboxylic acid, adipic acid so that amides are formed at both ends of each monomer, nylon 6 that may be made by a ring-opening polymerization of the 6-carbon cyclic amide, caprolactam, and nylon 7 that may be formed by polymerization of either 7-aminoheptanoic acid or enantholactam.

Nylons are designated by a numerical suffix that specifies the numbers of carbons donated by the monomers. For example, for nylons with a two-number designation, such as nylon 6,6 or nylon 6,12, the first number represents the number of carbons from the diamine monomer, and the second number represents the number of carbons from the diacid monomer. For nylons having a single number designation, such as nylon 6 or nylon 7, the number represents the number of carbon atoms in the repeating monomer units.

Nylon 7 is generally an aminocarboxylic acid based nylon fiber having properties that are comparable to or better than those of nylon 6 and nylon 6,6. For example, nylon 7 can provide improved textile properties compared to those of nylon 6 and nylon 6,6. These improved textile properties include higher melting temperature and reduced water absorption. However, there are lacking economically competitive methods for producing the monomers required for the production of nylon 7.

Therefore, there remains a need for methods of producing nylon 7 that are cost competitive with the production methods for producing nylon 6 and nylon 6,6. Methods for producing nylon 7 that are environmentally friendly and recycle waste materials are also desired.

SUMMARY

Nylon 7 may be produced from biomass derived 6-carbon hydroxymethyl furan compounds as the raw material. The hydroxymethyl furan compounds may be homologated to form an aldehyde that may be aminated to produce an amino carbonyl compound. By a first method, the amino carbonyl compound may be used as monomers in a polycondensation reaction to yield a polyamide. Treatment of the polyamide under catalytic hydrogenation/hydro-deoxygenation conditions may provide nylon 7. In another method, the amino carbonyl compound may be treated under catalytic hydrogenation/hydrodeoxygenation conditions to yield 7-aminoheptanoic acid that in turn, may be polymerized via polycondensation to yield nylon 7.

In an embodiment, a method for producing nylon 7 includes converting at least one furan compound of formula

wherein M1 is

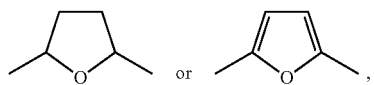

to an amino carbonyl compound of formula

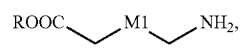

wherein R comprises —H, a alkyl, or a substituted alkyl, and converting the amino carbonyl compound to nylon 7.

In an embodiment, nylon 7 may be produced from waste stream products. The waste stream products include $CO_2$ and biomass. The method for producing nylon 7 includes converting biomass to hydroxymethyl furfural, and using the hydroxymethyl furfural and $CO_2$ as reactants for producing nylon 7.

DETAILED DESCRIPTION

Nylon 7 receives its numerical designation from the number of carbon atoms in its monomer units, wherein each monomer unit has seven carbons as illustrated below.

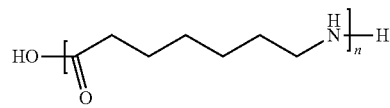

Nylon 7

As mentioned above, nylon 7 may be an optimal aminocarboxylic acid based nylon fiber, but production has been cost inhibitive in comparison to the cost of other nylons. In accordance with embodiments as discussed herein, nylon 7 may be produced by cost-competitive methods that are also environmentally friendly.

Figure 1:
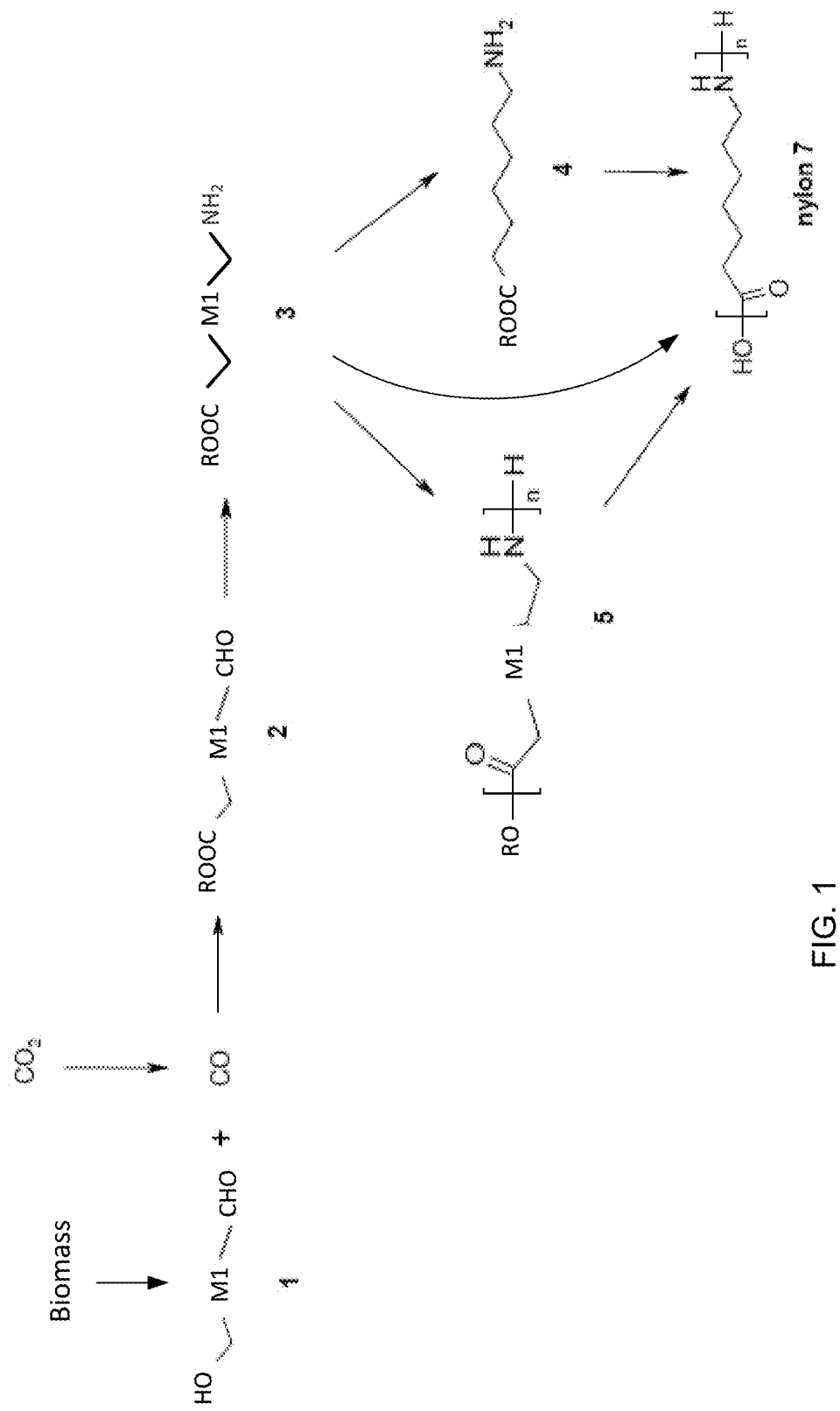
FIG. 1 depicts a general flow diagram for an illustrative method for the production of nylon 7 according to an embodiment.

A representation of a method for producing nylon 7 is depicted in FIG. 1. In an embodiment, furan compounds 1 of formula

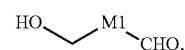

wherein M1 is

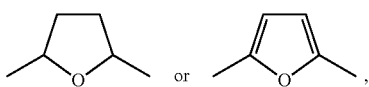 or may be converted to amino carbonyl compounds 3 of formula

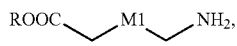

wherein R may be —H, an alkyl, or a substituted alkyl, and the amino carbonyl compounds may be converted to nylon 7. The amino carbonyl compounds 3 may be converted to nylon 7 by a hydrogenation-hydrodeoxygenation reaction that may result in the opening of the furan rings M1 and polymerization of the amino-carbonyl compounds.

As represented in FIG. 1, at least one furan compound 1 may be converted to an amino carbonyl compound 3 by converting the at least one furan compound

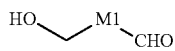

to an ester aldehyde or acid aldehyde, hereinafter referred to as aldehyde 2, of formula

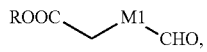

and aminating the aldehyde to produce the amino carbonyl compound 3.

At least one furan compound 1 may be a compound with only six carbons, and an additional carbon may be introduced into the furan compound to produce nylon 7. As represented in FIG. 1, this may be done via a homologation reaction with carbon monoxide. In an embodiment, a homologation of the furan compound 1 may include reacting the at least one furan compound with carbon monoxide in the presence of a catalyst and an aqueous solvent to produce the aldehyde 2. The catalysts may include, but are not limited to, palladium, rhodium, cobalt, iridium, nickel, ruthenium, platinum, or iron, or any combination thereof. Some examples of catalysts may include, but are not limited to, Pd(TPPTS)$_3$, Pd(TPPDS)$_3$, or Pd(TFPPDS)$_3$, or any combination thereof.

In an embodiment, the furan compound 1 may be homologated by mixing the at least one furan compound, carbon monoxide gas, Pd(TPPTS)$_3$ in deoxygenated and deionized water, and sulphuric acid in deoxygenated/deionized water, to produce a first mixture. The first mixture may be heated for a period of time, and at a temperature and pressure sufficient for homologization of the at least one furan compound to produce a second mixture containing the aldehyde 2. The second mixture may also contain 5-methylfurfural as a byproduct, and the aldehyde 2 may be extracted from the second mixture to separate the aldehyde from the 5-methylfurfural. In an embodiment where short chain nylon 7 polymers may be desired, the 5-methyl furfural byproduct and aldehyde 2 may be left combined, and in the subsequent amination steps as described below, 5-methylfurfural may be converted to 5-methyl furfurylamine, and in a further subsequent polycondensation step, as also described below, the 5-methyl furfurylamine may function as a chain terminator, thereby reducing nylon 7 polymer chain length.

In an embodiment wherein the aldehyde 2 may be an acid aldehyde (R is H), the acid-aldehyde may be converting to an ester-aldehyde (R is alkyl) by treating the acid-aldehyde with an alkyl alcohol in the presence of an acid catalyst. This may be done by treating the acid-aldehyde with methanol in the presence of toluenesulfonic acid catalyst.

The aldehydes 2 may be aminated to produce the amino carbonyl compounds 3 by any of several methods. In an embodiment, the aldehyde may be aminated by treating the aldehyde with an ammonia source in the presence of a catalyst. As an example, this may be carried out by treating the aldehyde with aqueous ammonium hydroxide in the presence of a nickel catalyst. In an alternative embodiment, the aminating may be carried out by treating the aldehyde with hydroxylamine to produce an oxime, and treating the oxime with hydrogen and a nickel catalyst to produce the amino carbonyl compound. In a further embodiment, the aminating may be carried out by treating the aldehyde with sodium cyanoborohydride, ammonium acetate, aqueous ammonium hydroxide, and alkyl alcohol. The alkyl alcohol may be, for example, methanol, ethanol, propanol, or butanol, or any combination thereof.

As also represented in FIG. 1, the hydrogenation-hydrodeoxygenation reaction of the amino carbonyl compounds 3 may proceed via at least one of several different pathways. In a first option, the ring-opening of the furan ring M1 may precede the polymerization to produce an intermediary 4, generally having a structure as represented by

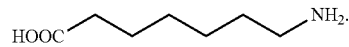

Alternatively, the polymerization may occur prior to the ring-opening of the furan ring M1 to produce an intermediary 5, generally having a structure as represented by

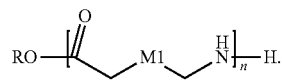

Lastly, the ring-opening of the furan ring M1 and the polymerization may occur simultaneously, going directly from the amino carbonyl compound 3 to nylon 7.

In an embodiment, the furan compound may be 5-hydroxymethylfurfural, wherein M1 is

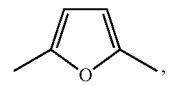

and the intermediaries may then be

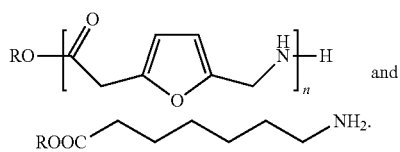

Alternatively, the furan compound may be 5-hdyroxymethyltetrahydrofuran-2-carbaldehyde, wherein M1 is

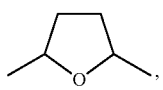

and the intermediaries may be

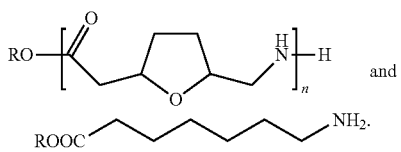

One type of hydrogenation-hydrodeoxygenation reaction may include treating the amino carbonyl compound 3 with a halide source and hydrogen gas in the presence of a catalyst. Since many usable metal catalysts are toxic, after the treating step, the catalyst may be removed, and the nylon 7 product may be precipitated by the addition of a suitable first solvent. Some examples of the first solvent may include water, methanol, ethanol, isopropanol, ethyl acetate, acetone and methyl ethyl ketone, diethyl ether, toluene, hexane, or heptane, or any combination thereof. This may be a single-pot reaction. The halide source may be at least one hydrogen halide, examples of which may include, but are not limited to hydrogen iodide, hydrogen bromide, or a combination thereof. Some examples of catalysts may include, but are not limited to, platinum, palladium, rhodium, ruthenium, nickel, cobalt, iron, molybdenum, iridium, rhenium, or gold, or any combination thereof. The catalyst may be mounted on a support, and support mounted catalyst may be removed from the reaction products by filtration.

In an embodiment, an additional solvent may also be used in the hydrogenation-hydrodeoxygenation reaction. The additional solvent may be a solvent in which the amino carbonyl compounds, the intermediary products, and nylon 7 are all soluble. Some examples of the additional solvent may include, but are not limited to, formic acid, acetic acid, propionic acid, butyric acid, dimethylformamide, dimethylacetamide N-methylpyrrolidinone, dimethylsulfoxide, phenol, xylenols, cresols, chlorophenols, resorcinol, or hexafluoroisopropanol, or any combination thereof.

Figure 2:
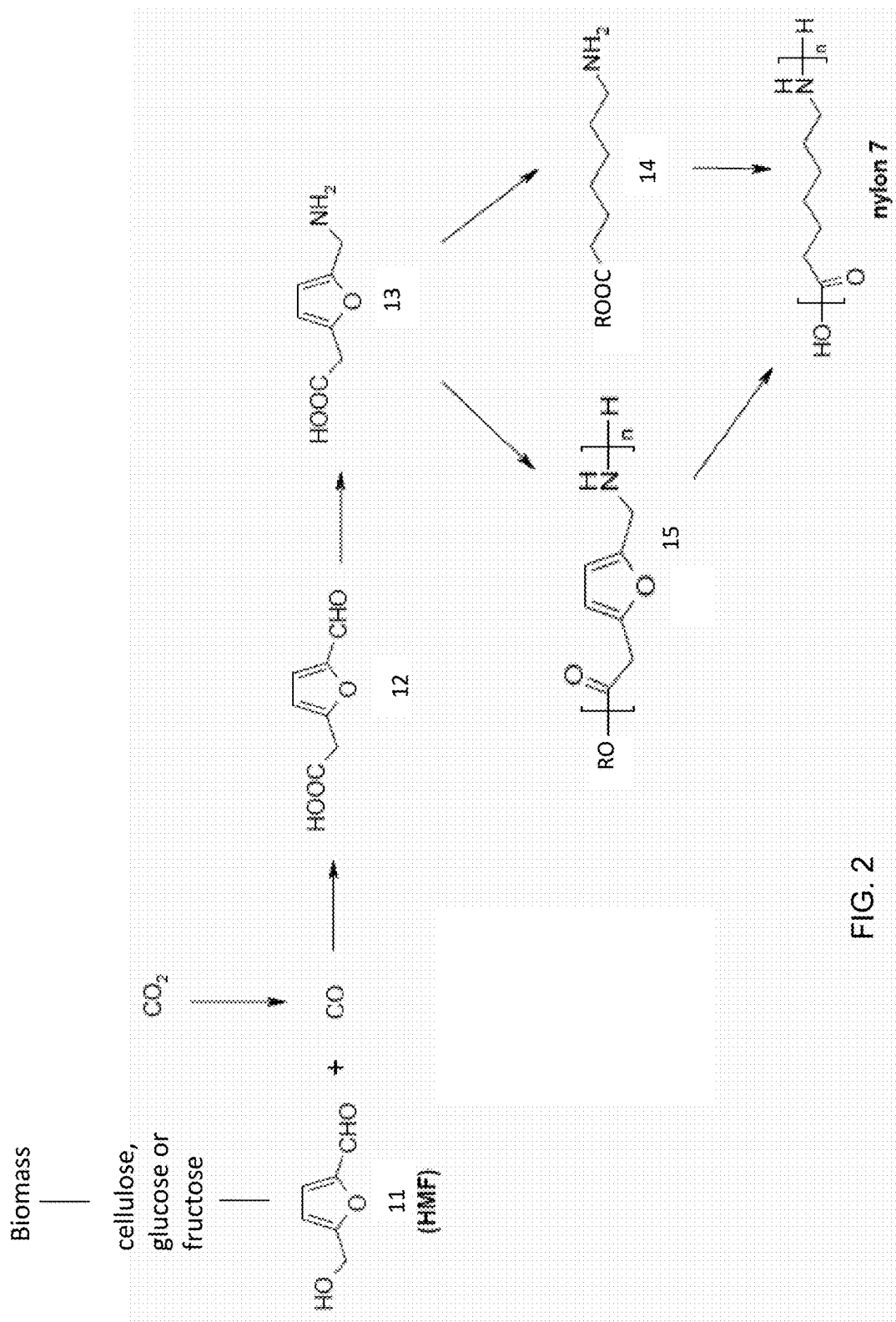
FIG. 2 depicts a diagram for an illustrative method for the production of nylon 7 from waste stream products according to an embodiment.

As represented in FIG. 2, a method for producing nylon 7 may include using hydroxymethylfurfural 11 as the starting material. The method may include homologation of the hydroxymethyl furfural 11 to produce 5-formyl-2-furanacetic acid 12, aminating the 5-formyl-2-furanacetic acid to produce [5-(aminomethyl)furan-2-yl]acetic acid 13, and hydrogenating-hydrodeoxygenating the [5-(aminomethyl) furan-2-yl]acetic acid to produce nylon 7.

Furan compounds 11 for producing nylon 7 may be obtained from biomass. In an embodiment, furan compounds 11 may be produced from biomass by isolating hexoses (glucose and/or fructose), cellulose, or any combination thereof from the biomass, and converting the hexoses, cellulose, or combination thereof to the furan compounds.

In an embodiment, nylon 7 may be produced from waste stream products. The waste stream products may include biomass and $CO_2$. The biomass may be converted to hydroxymethyl furfural, and the hydroxymethyl furfural and $CO_2$ may be used as reactants for producing nylon 7. The $CO_2$ may also be obtained from waste streams of a variety of other processes, such as, for example, combustion of coal or hydrocarbons, and the $CO_2$ may be reduced to CO. The biomass may be lignocellulosic biomass, and the biomass may be obtained from waste streams of a variety of other processes, such as, for example, waste wood chips and sawdust from lumber and paper production, corn stover, and sugarcane bagasse.

EXAMPLES

Example 1: Production of Nylon 7

Nylon 7 is produced from 5-hydroxymethylfurfural (HMF) 11. A mixture of palladium chloride (0.2 mmol), triphenylphosphine-3,3',3"-trisulfonic acid trisodium salt (TPPTS, 1.2 mmol), HMF (50 mmol), sulfuric acid (1.2 mmol) in deoxygenated/deionized water (130 mL) is treated with carbon monoxide gas (5 bar) while heating at about 70° C. in an autoclave for about 20 hours. The resultant mixture contains an approximately 3:1 mixture of the acid-aldehyde 12 and 5-methylfurfural. The mixture is neutralized by addition of aqueous sodium bicarbonate solution and extracted with ethyl acetate to remove the 5-methyl furfural. The aqueous phase is adjusted to pH of about 2 by addition of 5% hydrochloric acid solution saturated with sodium chloride, and is extracted with ethyl acetate. The organic phase is dried over magnesium sulfate and concentrated under reduced pressure to yield acid-aldehyde 12.

A solution of acid-aldehyde 12 in diethyl ether is cooled in an ice bath. A diethyl ether solution of diazomethane is added slowly until the yellow color persists. After being stirred for about 10 minutes, the ether is removed under reduced pressure to yield 5-formylfuran-2-acetic acid methyl ester.

A mixture of acid-aldehyde 12 (1 equivalent), hydroxylamine hydrochloride (1 equivalent), 10% aqueous sodium hydroxide solution (2.1 equivalents sodium hydroxide) and ethanol is heated at about 50° C. After about 1 hour, the mixture is treated with 10% hydrochloric acid (1.2 equivalents) and the solid is filtered to yield 5-formylfuran-2-acetic acid oxime.

Alternatively, a mixture of 5-formylfuran-2-acetic acid methyl ester (1 equivalent), hydroxylamine hydrochloride (1 equivalents), potassium acetate (1 equivalents), and 50% aqueous ethanol is heated at about 50° C. for about 1 hour. After cooling, the precipitate is filtered, washed with water and dried under reduced pressure to yield 5-formylfuran-2-acetic acid methyl ester oxime.

The oximes are converted to amino acids or amino esters. For example, a mixture of 5-formylfuran-2-acetic acid oxime, Raney nickel catalyst, and tetrahydrofuran as solvent, is treated with hydrogen gas (50 bar) in an autoclave for about 1 hour. The catalyst is removed by filtration and rinsed with tetrahydrofuran under argon. The combined filtrates are concentrated under reduced pressure to yield amino acid 13. Similarly, 5-formylfuran-2-acetic acid methyl ester oxime may yield methyl 5-(aminomethyl) furan-2-acetic acid methyl ester.

A mixture of amino acid 13 (1 equivalent), 5% palladium on silica (0.01 equivalent palladium) and acetic acid solvent is heated in an autoclave at about 160° C. while treating with hydrogen (50 atmospheres) for about 3 hours. The mixture is cooled, hydrogen iodide (1 equivalent) is added, and heating at about 160° C. while treating with hydrogen (50 atmospheres) is resumed for another 3 hours. After cooling, the mixture is filtered to remove the catalyst. The solvent is removed by distillation under reduced pressure to yield 7-aminoheptanoic acid. Similarly, methyl 5-(aminomethyl) furan-2-acetic acid methyl ester may yield methyl 7-aminoheptanoate.

Either 7-aminoheptanoic acid or methyl 7-aminoheptanoate is heated at about 270° C. for 5 hours to provide nylon 7.

Example 2: Generation of Nylon 7 Precursors from Waste Stream Products

Nylon 7 may be produced by the process described in Example 1 from 5-hydroxymethylfurfural derived from waste stream biomass, and carbon monoxide derived from waste stream carbon dioxide. Lignocellulosic biomass materials, such as corn stover, sugarcane bagasse, wood chips and sawdust will be obtained from waste streams. The biomass will be processed to isolate hexoses, glucose and fructose from the biomass. The hexoses will be dehydrated to form 5-hydroxymethylfurfural. Carbon dioxide will be retrieved from waste exhaust from an electricity generation plant, or other exhaust stream. The carbon dioxide will be reduced to form carbon monoxide.

Example 3: Comparison of Nylon 7 with Nylon 6 and Nylon 6,6

The following table provides a comparison of the physical properties of nylon 7 as compared with those of nylon 6 and nylon 6,6.

TABLE 1

Comparison of Physical and textile properties of nylons 6, 7, and 6,6

| Property | Nylon 6 | Nylon 7 | Nylon 6,6 |
|---|---|---|---|
| Tenacity, cN/dtex | 8.0-8.5 | 8.1-8.5 | 8.2-8.7 |
| Wet strength, % of dry | 81 | 92 | 85 |
| Elongation at break, % | 24 | 14-16 | 18 |
| Elastic modulus, cN/dtex* | 41 | 46-49 | 54 |
| Wet modulus, % of dry** | 27 | 62 | 31 |
| Boil-off shrinkage, % | 12 | 8-10 | 10 |
| density, g/cm$^3$ | 1.14 | 1.10 | 1.14 |
| melting point, ° C. | 214-220 | 225-233 | 255-260 |
| Water absorption, % | | | |
| at 65% R.H. | 4.3 | 2.8 | 4-4.5 |
| at 100% R.H. | 9-10 | 5 | 9-10 |

*At 1% elongation
**In 25° C. water.

The examples demonstrate that nylon 7 has properties that are comparable to, or better than, those of nylon 6 and nylon 6,6. In addition, nylon 7 may be produced from waste products in only a few process steps with yields of up to about 100%, thereby reducing the cost of production of nylon 7, as well as the need for petrochemically derived raw materials.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for producing nylon 7 from waste stream products, the waste stream products comprising $CO_2$ and biomass, the method comprising:
    isolating hexoses, cellulose, or combination thereof from the biomass;
    converting the hexoses, cellulose, or combination thereof to hydroxymethyl furfural;
    performing an homologation on the hydroxymethyl furfural with CO to produce 5 formyl-2-furanacetic acid;
    aminating the 5-formyl-2-furanacetic acid to produce [5-(aminomethyl)furan-2-yl]acetic acid; and
    hydrogenating-hydrodeoxygenating the [5-(aminomethyl)furan-2-yl]acetic acid to produce nylon 7.

2. The method of claim 1, wherein the hydrogenation-hydrodeoxygenation reaction comprises treating the [5-(aminomethyl)furan-2-yl]acetic acid with a halide source and hydrogen gas in the presence of a catalyst.

3. The method of claim 2, wherein treating comprises treating in the presence of a catalyst comprising platinum, palladium, rhodium, ruthenium, nickel, cobalt, iron, molybdenum, iridium, rhenium, gold, or any combination thereof.

4. The method of claim 2, wherein the hydrogenation-hydrodeoxygenation reaction comprises producing intermediary products including

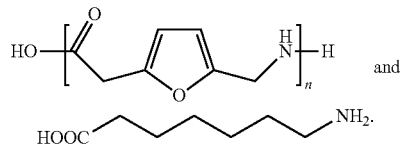

5. The method of claim 1, further comprising precipitating the nylon 7 from a solvent.

6. The method of claim 1, wherein the homologation reaction comprises reacting the hydroxymethyl furfural with the CO in the presence of a catalyst and an aqueous solvent.

7. The method of claim 6, wherein reacting the hydroxymethyl furfural with the CO comprises reacting in the presence of $Pd(TPPTS)_3$, $Pd(TPPDS)_3$, $Pd(TFPPDS)_3$, or a combination thereof.

8. The method of claim 1, wherein the homologation reaction comprises:
    mixing CO gas, $Pd(TPPTS)_3$ in deoxygenated and deionized water, hydroxymethyl furfural, and sulphuric acid in deoxygenated/deionized water to produce a first mixture; and
    heating the first mixture for a period of time, temperature and pressure sufficient for homologization of the hydroxymethyl furfural to produce a second mixture.

9. The method of claim 1, wherein aminating the 5-formyl-2-furanacetic acid comprises treating the 5-formyl-2-furanacetic acid with one or more of an ammonium cation source and aqueous ammonium hydroxide in the presence of a catalyst.

* * * * *